(12) United States Patent
Rizzi

(10) Patent No.: US 6,926,869 B2
(45) Date of Patent: Aug. 9, 2005

(54) APPARATUS FOR CARBAMATE DECOMPOSITION AND AMMONIA AND CARBON DIOXIDE STRIPPING FROM UREA SOLUTIONS CAPABLE OF 180 DEGREE INVERSION ABOUT A HORIZONTAL AXIS

(75) Inventor: Enrico Rizzi, Grandate (IT)

(73) Assignee: Urea Casale S.A., Lugano-Besso (CH)

( * ) Notice: Subject to any disclaimer, the term of this patent is extended or adjusted under 35 U.S.C. 154(b) by 436 days.

(21) Appl. No.: 09/970,975

(22) Filed: Oct. 5, 2001

(65) Prior Publication Data

US 2002/0041838 A1 Apr. 11, 2002

(30) Foreign Application Priority Data

Oct. 9, 2000 (EP) ............................................ 00121953

(51) Int. Cl.$^7$ ................................................. B01J 8/02
(52) U.S. Cl. ....................... 422/144; 422/188; 422/197; 422/198
(58) Field of Search ................................. 422/144, 188, 422/197, 198, 211, 220

(56) References Cited

U.S. PATENT DOCUMENTS 3,922,147 A * 11/1975 Sze et al. .................. 422/193
5,176,800 A * 1/1993 Zardi et al. .................. 203/31
5,888,460 A * 3/1999 Zardi et al. ................. 422/193
6,010,669 A 1/2000 Miola et al. ................. 422/241

FOREIGN PATENT DOCUMENTS

| EP | 0 306 614 A2 | * 3/1989 | ......... C07C/126/02 |
| EP | 0 435 008 A1 | 7/1991 | ......... C07C/273/04 |
| EP | 0 464 307 A1 | 1/1992 | ......... C07C/273/04 |

* cited by examiner

*Primary Examiner*—Kevin P. Kerns
(74) *Attorney, Agent, or Firm*—Sughrue Mion, PLLC

(57) ABSTRACT

An apparatus (1) for carbamate decomposition and ammonia and carbon dioxide stripping from urea solutions, wherein a stripper (2) including a substantially cylindrical shell (3), which can be fitted onto a structure (6) for supporting the shell (3) in two distinct vertical positions rotated by 180 ° with respect to a horizontal symmetry axis (x-x) of the stripper. By virtue of the symmetrical design of stripper (2), the operation and the associated connections of the upper and lower portions are effectively interchangeable, thereby providing a substantial increase in the service life of the stripper when the stripper is rotated so as to bring a corrosion damaged upper part down, at the bottom of the apparatus, and bring the opposed, not yet damaged corresponding area up.

5 Claims, 4 Drawing Sheets

# US 6,926,869 B2

APPARATUS FOR CARBAMATE DECOMPOSITION AND AMMONIA AND CARBON DIOXIDE STRIPPING FROM UREA SOLUTIONS CAPABLE OF 180 DEGREE INVERSION ABOUT A HORIZONTAL AXIS

DESCRIPTION

1. Field of Application

In its broader, aspect, the present invention relates to the recovery of carbamate and unreacted free ammonia from the aqueous urea solution that is produced by the reaction between ammonia and carbon dioxide; in the following description such aqueous urea solution will also be called ureic solution.

More in particular, the present invention relates to a separation of unreacted substances from the aqueous urea solution which becomes thus concentrated, obtained through decomposition of the carbamate (intermediate product of the urea synthesis reaction) and stripping of the unreacted ammonia and carbon dioxide, for example with a flow of carbon dioxide that is then used as reactant for the urea synthesis itself.

More specifically, but not exclusively, the present invention relates to an improved apparatus for carrying out the stripping of the above components from the aqueous urea solution containing them, which apparatus is of the type comprising:

a stripper including a substantially cylindrical shell closed at opposed ends by respective bottom and equipped in the proximity thereof with inlet and outlet openings of stripping fluids, heat exchange and control means and devices for the stripping step;

a structure for supporting such shell in vertical position.

The invention also relates to a method for increasing the service life of an apparatus of the above mentioned type and the following description is made with reference to this specific field of application with the only purpose of simplifying the exposure thereof.

2. Prior Art

As it is well known in this specific technical field, the completion of the urea synthesis step consists in the separation and recycle to the synthesis section of the unreacted substances from the aqueous ureic solution that comprises them; to such end, stripping apparatuses are used that are associated to the synthesis reactors and preferably operates practically at the same pressure of the respective reactors. From a mere structural point of view, these apparatuses are comparable to large heat exchangers of the tube bundle type, supported in vertical position; it is inside the tubes that the actual "stripping" operation takes place, that is to say that treatment of the urea aqueous solution leaving the reactor by which the major portion of unreacted ammonia and $CO_2$ is separated (stripped) therefrom, thus obtaining concentrated urea.

The separation of unreacted ammonia and $CO_2$ occurs by heating with steam the urea aqueous solution and, in the so called "$CO_2$ stripping" cases, even adding $CO_2$ as a stripping agent.

In the urea processes with total recycle, in particular those where the $CO_2$ fed to the synthesis reactor is used as a stripping agent, the tube bundle heat exchanger wherein the stripping step takes place, is the apparatus in which corrosion phenomena are most likely to occur.

More precisely, the most prone area to corrosion is the upper part of the stripper, near the upper end of the tubes of the tube bundle heat exchanger. In fact, inside the upper part of the tubes, the evaporation phenomenon is more severe, with formation of $NH_3+CO_2$+water vapours, which exercise a corrosive and erosive action of the passivating film which normally coats and protects the inner walls of said tubes.

More in particular, in their upper part the walls of the tubes of the tube bundle get thinner and thinner due to the corrosion, and, for this reason, a replacement of the complete stripper will be needed, or else a very expensive maintenance which generally foresees a shortening of the tube bundle heat exchanger, in order to eliminate the damaged upper part.

Because of this corrosion phenomenon, the average lifetime of the stripping apparatus is about 10–12 years, whereas in most cases a lot of other parts of the apparatus, in particular the strippers' shell, are still validly useable.

Special materials have been studied in order to realize such an apparatus and to limit this corrosion phenomenon. To date, though, it is not possible to eliminate the corrosion.

The technical problem at the basis of the present invention is that of devising an improved apparatus in order to allow the separation of carbamate and the stripping of ammonia and carbon dioxide from the urea aqueous solutions, which has such structural and functional features as to provide an increase of service life of the apparatus itself, overcoming the limitations of the solution nowadays provided by the prior art.

SUMMARY OF THE INVENTION

The resolutive idea at the basis of the present invention is that of foreseeing an overturning of 180° of the stripper so as to bring the damaged upper part down, at the bottom of the apparatus, and bring the opposed, not yet damaged corresponding area up. In this way, the service life of the stripper is practically doubled.

Based upon this idea, the aforesaid technical problem is solved by an apparatus of the above-indicated type and defined by the claims, attached hereto.

The invention relates moreover to a method for increasing the service life of an apparatus for carbamare decomposition and unreacted ammonia and carbon dioxide stripping from aqueous urea solutions.

The features and advantages of the apparatus and of the method according to the invention will appear more clearly from the following description of a non-limiting and indicative embodiment thereof, with reference to the attached drawings.

In such drawings:

DETAILED DESCRIPTION

Figure 1:
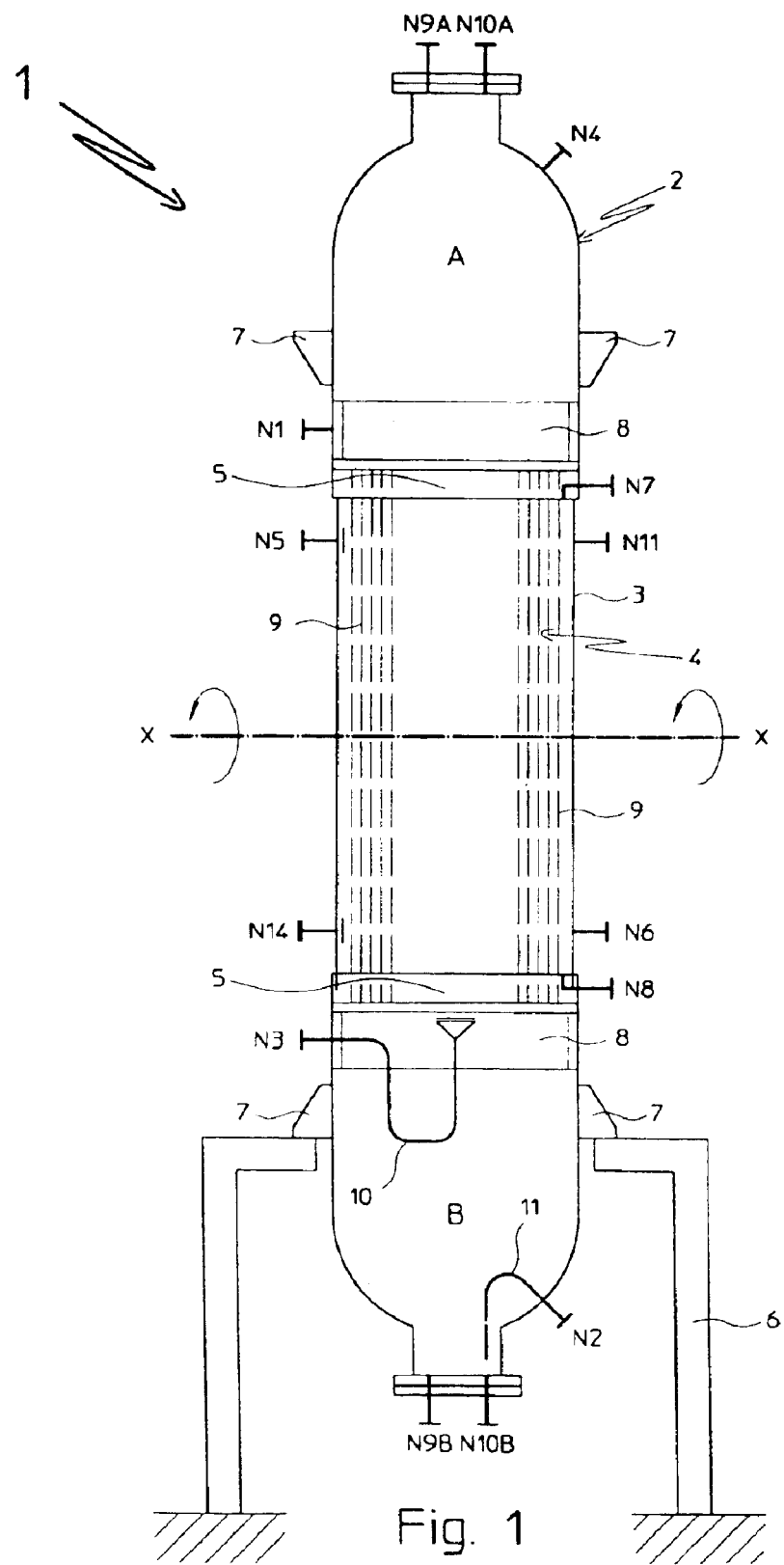
FIG. 1 shows a schematic view of an apparatus according to the invention in a first condition of use, for carbamate stripping from urea aqueous solutions.

With reference to the above mentioned figures, with numeral 1 there is schematically indicated in its whole an apparatus realized according to the present invention for decomposing the carbamate and stripping unreacted ammonia and carbon dioxide from urea aqueous solutions that contain them.

Obviously, such apparatus is associated with a urea synthesis reactor, not shown as it is of conventional type, which feeds apparatus 1 with a synthesis ureic solution. Such a solution is a ureic aqueous solution comprising urea, carbamate and unreacted ammonia.

Apparatus 1 comprises a stripper 2, including a substantially cylindrical shell 3. Shell 3 is closed at its opposite ends by respective bottoms A, B.

Each of the bottoms A, B comprises a cylindrical portion, fitted on the corresponding end of the shell 3, and a spherical closing cap. At the top of the spherical cap, the bottoms are provided with respective passages, so-called "manholes".

Near the bottoms A, B various openings are further provided for the inlet and/or outlet of stripping fluids, which will be described in detail hereinbelow.

Inside the shell 3, heat exchange means and devices are arranged. Such means are represented by a tube bundle type heat exchanger 4, supported inside the shell by respective tube plates 5 located at the lower and upper bottoms A, B. Through said manholes it is possible to reach such tube plates 5 during erection or maintenance.

Figure 3:
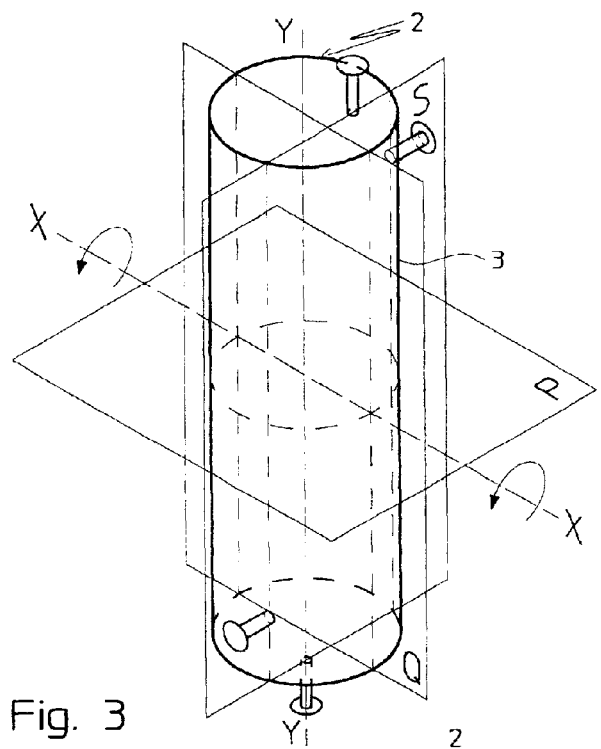
FIG. 3 shows a schematic view of a detail of the apparatus of FIG. 1.

For supporting the shell 3 in vertical position, the apparatus 1 further has a supporting structure 6. The longitudinal axis y-y of the shell 3 extends thus in a vertical direction (FIG. 3).

Figure 5:
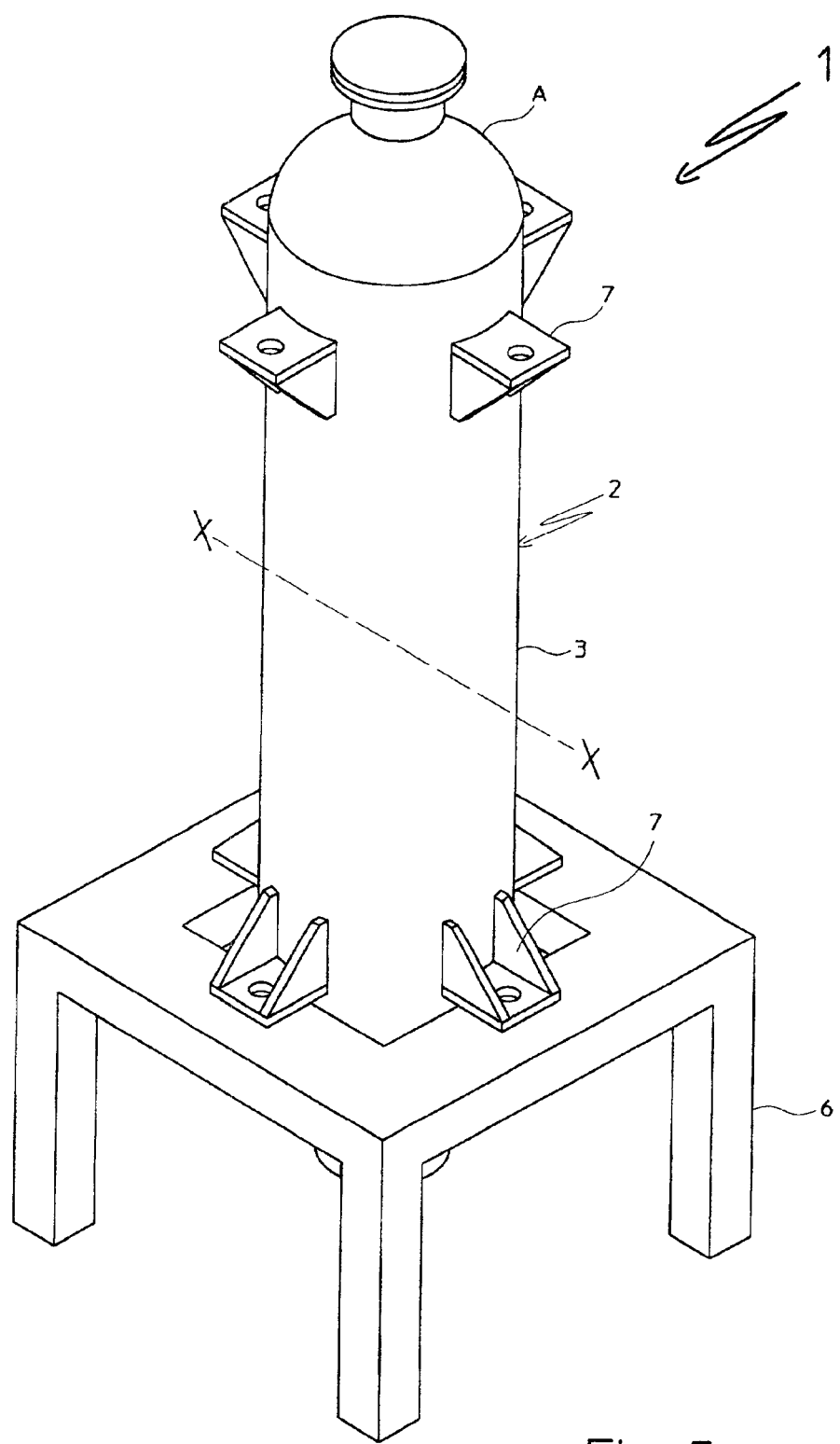
FIG. 5 shows a perspective view of the apparatus of FIG. 1.

In particular, the shell 3 is provided with support elements 7, for example supporting saddles, which are fixed to the structure 6 as shown in FIG. 5.

With reference to FIG. 1, the ureic solution comprising: urea, carbamate, free ammonia and water, coming from a urea synthesis reactor, not shown as conventional, is fed into the stripper 2 through a nozzle N1, arranged in the cylindrical portion of the bottom A.

The ureic solution, which needs to be concentrated, is distributed onto the upper tube plate 5 through a distribution box 8 and is made to fall down inside the tubes 9 with a film-flow motion through sleeves (not shown) put onto the tubes 9 of the heat exchanger 4.

The box 8 is fastened to the cylindrical portion of the corresponding bottom A and is for example formed by a box of welded metal sheets. The task of such box 8 is that of distributing the process ureic solution onto the underlying tube plate 5.

From a nozzle N3, located in the lower part of the shell 2, $CO_2$ is fed, which is used a stripping agent and, by making ammonia evaporate, promotes the decomposition of the carbamate. In order to have a good distribution of the gases, inside the lower bottom B a $CO_2$ distributor is mounted, which is connected to the nozzle N3 through a connection tube 10. The $CO_2$ distributor is inserted in the fluid distribution box 8.

The evaporation and decomposition heat of carbamate is provided by water steam condensing outside the tubes 9. The water steam enters through a nozzle N5 located below the upper tube plate 5 at a minimum distance therefrom. Once condensed, the steam is discharged from the lower part of the tube bundle through a nozzle N6, located little above the lower tube plate 5.

From a nozzle N4, located onto the spherical cap upper bottom A of the shell 3, the ammonia vapours exit together with stripping $CO_2$ and $CO_2$ and water that are produced by the evaporation and dissociation of carbamate.

The so concentrated urea solution is discharged, while controlling its level, from the lower part of the stripper 2 through a nozzle N2, located in the spherical cap lower bottom B and connected to a U-shaped pipe 11.

Always on the lower bottom of the shell 3, suitable nozzles are provided located at the manhole and connected to a level control device/instrument. If the level control instrument of the process solution is of differential type (ΔP Cell) in view of particular requirements, two nozzles N9B and N10B are obtained in the manhole of the lower bottom B, one for each arm of the control instrument. On the contrary, if the level control instrument is of radioactive type, instead of the two aforesaid nozzles N9B and N10B, a single nozzle is provided in the cylindrical portion of the lower bottom B, through which the radioactive probe can be introduced in the shell 3.

As the tube bundle needs to be protected by possible overpressures, a nozzle N11 is provided, located below and at a minimum distance from the upper tube plate 5, onto which a safety valve is applied.

The so-called "drain" and "vent" of the tube bundle are obtained from the tube plates and are indicated with N8 and N7, respectively.

On the tube bundle, near the lower tube plate 5, a further nozzle N14 is provided, from which the condensate can be extracted as an alternative to nozzle N6.

Advantageously, according to the present invention, the shell 3 of the stripper 2 may be fitted on said structure 6 in two distinct vertical positions rotated by 180° with respect to a horizontal symmetry axis x-x of the stripper 2. In this respect, a first vertical position or condition of use is the one illustrated in FIG. 1, whereas a second vertical position is the one illustrated in FIG. 2.

In particular, the apparatus 1 according to the invention is suitably realized in such a way that the stripper 2 may be rotated without making modifications to the connecting circuits to external units.

For example, inside the shell 3 a double distribution box 8 of the ureic solution is provided, whereas, in at the bottoms A, B, absolutely symmetrical connection nozzles are provided.

Figures 4A, 4B, 4C:
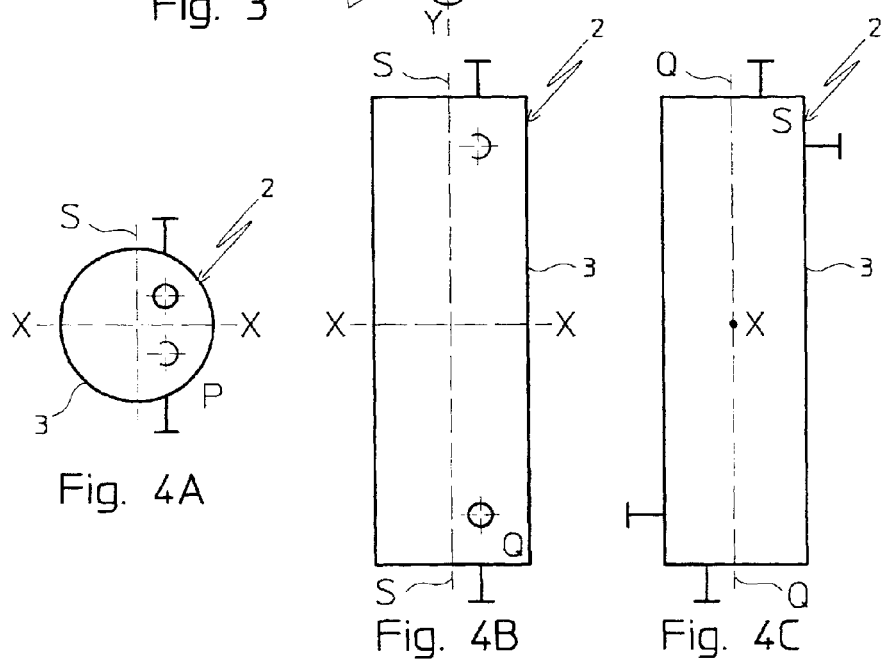
FIG. 4A shows a schematic view from above and FIGS. 4B and 4C respective schematic side views of the detail of FIG. 3.

As shown in FIGS. 3 and 4, the stripper 2 is symmetrical with respect to a horizontal symmetry axis x-x. Such symmetry axis x-x is defined by the intersection of a horizontal middle plane P with a vertical diametral plane Q of the stripper 2. By "diametral plane" it is intended to mean the plane that comprises the axis of the stripper 2 passing through the centre of the shell 3 (indicated with y-y in FIG. 3).

The rotation of the stripper 2 into the two distinct vertical positions occurs with respect to such symmetry axis x-x.

Advantageously, in the stripper 2 homologous nozzles are provided, which lay on planes S perpendicular to the plane Q and equidistant from that one. By "homologous nozzles" it is intended to mean pairs of nozzles that, after a 180° rotation of the stripper 2, can carry out the same task as will be clearer in the description hereinbelow.

In other words, the above-described nozzles are advantageously provided in symmetrical pairs with respect to axis x-x. Respective symmetrical pairs of nozzles lay on corresponding planes S parallel to each other and to the generatrix of the shell 3, indicated by the longitudinal axis y-y thereof, and perpendicular with respect to the plane Q. The nozzles of a respective pair are therefore symmetrical with respect to the point of intersection between the symmetry axis x-x and the corresponding lying plane S of the nozzles.

Figure 2:
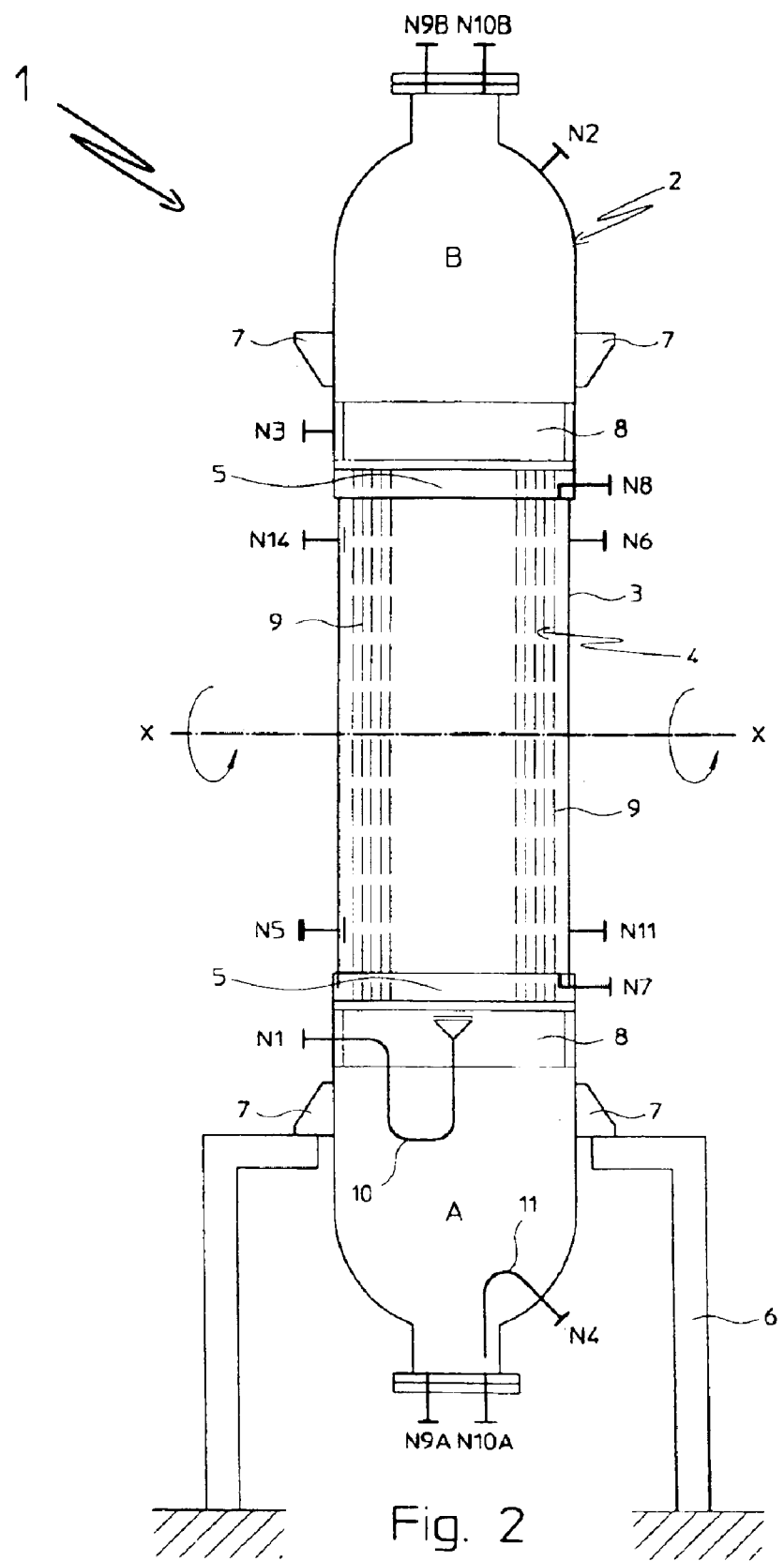
FIG. 2 shows a schematic view of the apparatus of FIG. 1 in a second condition of use.

With reference to FIG. 2, the structure of the apparatus 1 is further discussed, for a better understanding of the interchangeability of the upper and lower surfaces of stripper 2.

The process ureic solution flows inside the tubes 9 of the tube bundle through the nozzle N3. On the outer wall of the tubes 9 the condensation of water steam takes place in order to provide heat to the process ureic solution.

The nozzle N3 is located onto the cylindrical portion of the upper bottom B and is in fluid communication with the fluid distribution box 8 arranged inside said bottom B.

The steam that is set free from the process ureic solution is discharged through a nozzle N2 in the spherical cap portion of the upper bottom B.

The $CO_2$ used as stripping agent is introduced in the bottom A of stripper 2 through a nozzle N1 formed in the cylindrical portion of said bottom. Nozzle N1 is connected through the duct 10 to the $CO_2$ distributor located inside the lower bottom A and inserted in the fluid distribution box 8.

The process ureic solution is collected on the lower bottom A and is discharged through a nozzle N4 formed, in turn, in said bottom. Should the level control instrument for the process solution be for specific requirements of differential type ($\Delta P$ Cell), then, in the manhole of the lower bottom A two further nozzles N9A and N10A are formed, a respective one for each arm of the control instrument.

Should the level control instrument be on the contrary of a radioactive type, a single nozzle is provided in the cylindrical portion of the lower bottom A instead of said nozzles N9A and N10A, through which a radioactive probe can be introduced in the shell 3.

The heating water steam is introduced into the shell 3 outside the tubes 9 of the tube bundle, through a nozzle N6, located at a minimum distance from the upper tube plate 5.

The condensate will be extracted from the lower portion of the tube bundle through nozzle N5, located above the lower tube plate 5. As an alternative to nozzle N5, the condensate may even be withdrawn from nozzle N11.

On the tube plate, just below the upper tube plate 5, a nozzle N14 is provided, to which a safety valve protecting the bundle from a possible overpressure is connected.

The so-called "drain" and "vent" of the tube bundle are obtained by the tube plates and are indicated with N7 and N8 respectively.

In view of this description and FIG. 2, it is clear that, following an arrangement rotated by 180° of stripper 2 with respect to the condition of use of FIG. 1, nozzle N2 can be converted into nozzle N4 by simply changing the inner connections. The nozzle indicated with N3 can in turn be again employed as nozzle N1. The same applies for the other pairs of nozzles: N5/N14, N6/N11, N7/N8, N9B/N9A and N10B/N10A. To this purpose, the orientation of such nozzles is such that, after the overturning has taken place, their flanges can be connected to the corresponding feeding/discharge lines remained fixed.

Furthermore, the distribution box 8 is provided at both bottoms A, B, and the supporting members 7 are advantageously arranged outside the shell in the proximity of the bottoms A and B, in a symmetrical position with respect to the symmetry axis x-x of stripper 2.

Analogously, the heat exchange and control means and devices for the stripping step, and the connection elements between the nozzles and the corresponding inner portions of stripper 2, are advantageously arranged symmetrically with respect to the symmetry axis x-x of the stripper 2.

Therefore, the apparatus 1 according to the present invention may be turned over without requiring heavy modifications to the connection pipelines.

As the nozzle N3 on the lower bottom B positioned as in FIG. 1 is usually used to feed the stripping CO, the orientation of the nozzles N1, N3 should be such as to let the downwards rotated nozzle (N1), after a 180° overturning (FIG. 2), face the flange of the $CO_2$ tube (not shown) and the upwards rotated nozzle (N3) face the flange of the tube (not shown) that carries the process ureic solution.

In this way, when process solution flows through nozzle N1 (FIG. 1), the manhole has a blind flange, and as a consequence the corresponding box 8 accomplishes its task of distributing the ureic solution. When, on the contrary, through the same overturned nozzle N1 $CO_2$ is made to flow (FIG. 2), the manhole will be open in such a way as to connect the nozzle N1 with the connection tube 10 for $CO_2$ adduction arranged at the lower head.

Analogously, the nozzle N4 through which the steam is usually discharged from the upper bottom, is symmetrical with respect to the nozzle N2 of the lower bottom through which the collected ureic solution is discharged (FIG. 1). Also in this case, after having turned the stripper 2 over (FIG. 2), both nozzles face the ureic solution supply line and the steam discharge line, respectively.

Preferably, both nozzles N2 and N4 have been provided on the spherical cap portions of the bottoms A and B, so as not to form any nozzle on the flanges of the manholes in order to allow an easier inspection of the heat exchange heads. Obviously, however, nothing prevents from providing such nozzles on the manhole flanges.

Once the steam discharge nozzle N4 has been turned downwards, it is connected to the U-shaped pipe 11 dipping in the well of the lower manhole in such a way as to adjust the level of the process solution on all the selected range independently from the height of the nozzle itself.

For sake of completion, it is noted that the nozzles provided for the level control are provided both on the lower portion and on the upper portion. Those provided on the upper portion shall be provided with a blind flange.

What is claimed is:

1. Apparatus (1) for carbamate decomposition and ammonia and carbon dioxide stripping from urea solutions, of the type comprising:

a stripper (2) including a substantially cylindrical shell (3) closed at opposed ends by respective bottoms (A, B) and equipped in the proximity thereof with inlet and outlet openings (N1, N2, N3, N4, N5, N6) of stripping fluids, and a heat exchanger (4);

a structure (6) for supporting said shell (3) in a vertical position;

characterized in that the shell (3) of the stripper (2) is further externally equipped with support elements (7) so that the stripper (2) can be fitted onto said structure (6) in two distinct vertical positions rotated by 180° with respect to a horizontal axis of symmetry (x-x) of said stripper.

2. Apparatus according to claim 1, characterized in that said inlet and outlet openings (N1, N2, N3, N4, N5, N6) of the stripping fluids are symmetrical in the stripper (2) with respect to said symmetry axis (x-x).

3. Apparatus according to claim 1, characterized in that said support elements (7) are arranged, in the proximity of said bottoms, symmetrically with respect to the symmetry axis (x-x).

4. Apparatus according to claim 1, characterized in that said heat exchanger (4) is arranged in said cylindrical shell symmetrically with respect to said symmetry axis (x-x).

5. Apparatus according to claim 1, characterized in that said inlet and outlet openings (N1, N2, N3, N4, N5, N6) of the stripping fluids are nozzles symmetrically arranged with respect to said symmetry axis (x-x), in which respective symmetrical pairs of nozzles lay on corresponding planes (S) parallel to each other and perpendicular with respect to a diametral vertical plane (Q) of the stripper, the nozzles of a respective pair being symmetrical with respect to the point of intersection between said symmetry axis (x-x) and the corresponding lying plane (S) of the nozzles.

* * * * *